US00PP30995P2

(12) United States Plant Patent
Smit

(10) Patent No.: US PP30,995 P2
(45) Date of Patent: Oct. 29, 2019

(54) **X*GASTERALOE* PLANT NAMED 'MOROMBE'**

(50) Latin Name: **x*Gasteraloe* hybrid**
Varietal Denomination: Morombe

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 15/932,791

(22) Filed: Apr. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 6/00
See application file for complete search history.

(56) References Cited

PUBLICATIONS

UPOV PLUTO Plant Variety Database Record Detail, Morombe, Oct. 16, 2016.*

* cited by examiner

*Primary Examiner* — Keith O. Robinson

(57) ABSTRACT

A new cultivar of x*Gasteraloe* plant named 'Morombe' that is characterized by green leaves with green-white orbicular dots, leaf margins with white teeth and a basal rosette plant shape.

1 Drawing Sheet

Botanical classification: x*Gasteraloe* hybrid.
Variety denomination: 'Morombe'.

BACKGROUND OF THE INVENTION

The present invention relates to a new and distinct cultivar of x*Gasteraloe* plant botanically known as x*Gasteraloe* hybrid and hereinafter referred to by the cultivar name 'Morombe'.

'Morombe' originated from the crossing of the female or seed parent, Gasteria 'Royal Wolfgang' (U.S. Plant Pat. No. 25,667) with the male or pollen parent, an unnamed *Aloe aristata* cultivar. The crossing was conducted in 2010 in Sappemeer, Netherlands. The resulting seeds were subsequently planted and grown. The cultivar 'Morombe' was selected by the inventor in 2013 in a controlled environment as a single plant within the progeny of the stated cross in a cultivated area of Sappemeer, Netherlands.

Asexual reproduction of the new cultivar 'Morombe' first occurred by leaf cuttings in 2013 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new x*Gasteraloe* cultivar 'Morombe'. These traits in combination distinguish 'Morombe' as a new and distinct cultivar apart from other existing varieties of x*Gasteraloe* known by the inventor.

1. x*Gasteraloe* 'Morombe' exhibits green leaves with green-white orbicular dots.
2. x*Gasteraloe* 'Morombe' exhibits leaf margins with white teeth.

3. x*Gasteraloe* 'Morombe' exhibits a basal rosette plant shape.

The closest comparison cultivars are Aloe 'Tiki Zilla' (U.S. Plant Pat. No. 25,343) and Aloe 'Cosmo' (not patented). 'Morombe' is distinguishable from 'Tiki Zilla' by the following characteristics:

1. x*Gasteraloe* 'Morombe' exhibits longer and thinner leaves than the leaves of 'Tiki Zilla'.
2. x*Gasteraloe* 'Morombe' exhibits a larger number of teeth on the leaf margins than the number of teeth on the leaf margins of 'Tiki Zilla'.
3. x*Gasteraloe* 'Morombe' exhibits a more erect growth habit than the growth habit of 'Tiki Zilla'.

'Morombe' is distinguishable from 'Cosmo' by the following characteristics:

1. x*Gasteraloe* 'Morombe' exhibits a more open plant habit than the plant habit of 'Cosmo'. In contrast, the plant habit of 'Cosmo' is more compact.
2. x*Gasteraloe* 'Morombe' exhibits leaves with a large number of green-white orbicular dots. In contrast, 'Cosmo' has a fewer number of white dots.

'Morombe' can also be compared to the co-pending plant patent application of x*Gasteraloe* 'Kyaka' (U.S. application Ser. No. 15/932,816). 'Morombe' is distinguishable from 'Kyaka' by the following characteristics:

1. x*Gasteraloe* 'Morombe' exhibits leaves with smaller grey-green orbicular dots than the dots on the leaves of 'Kyaka'.
2. x*Gasteraloe* 'Morombe' exhibits leaf margins with longer teeth than the teeth on the leaf margins of 'Kyaka'.
3. x*Gasteraloe* 'Morombe' exhibits leaves that are longer and wider than the leaves of 'Kyaka'.

'Morombe' is distinguishable from the female parent plant, by the following characteristics:

1. x*Gasteraloe* 'Morombe' exhibits green leaves. The leaves of the female parent plant are dark green to blue-green.
2. x*Gasteraloe* 'Morombe' exhibits leaves with smaller green-white orbicular dots than the female parent plant. In contrast, the leaves of the female parent plant have larger orbicular white dots.

'Morombe' is distinguishable from the male parent plant by the following characteristics:

1. x*Gasteraloe* 'Morombe' exhibits green leaves. The leaves of the male parent plant are darker green in color.
2. x*Gasteraloe* 'Morombe' exhibits leaves with smaller green-white orbicular dots than the male parent plant. In contrast, the leaves of the male parent plant have larger orbicular white dots.

BRIEF DESCRIPTION OF THE DRAWING

The accompanying photograph illustrates the distinguishing traits of x*Gasteraloe* 'Morombe'. The photograph shows an overall view of an 18 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new x*Gasteraloe* cultivar named 'Morombe'. Data was collected in Sappemeer, Netherlands from 18 month old plants grown in a glass greenhouse in 10.5 cm. diameter containers. The time of year was Winter and the temperature range was 18-20 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Morombe' has not been tested under all possible conditions and phenotypic differences may be observed with variations in environmental, climatic, and cultural conditions, however, without any variance in genotype.

Botanical classification: x*Gasteraloe* hybrid 'Morombe'.

Annual or perennial: Perennial.

Parentage: 'Morombe' is a hybrid of the female parent, Gasteria 'Royal Wolfgang' and the male parent, an unknown *Aloe aristata* cultivar.

Plant type: Potted plant.

Growth habit: Basal rosette.

Plant shape: Globe shaped.

Suitable container size: 7 cm. pots or larger.

Plant height: 19.1 cm.

Plant width: 23.4 cm.

Vigor: Moderate.

Low temperature tolerance: 10° Centigrade.

High temperature tolerance: 35° Centigrade.

Propagation: Leaf cuttings and micro-propagation.

Time to initiate roots (summer): 14 days at 20° C.

Time to initiate roots (winter): 21 days at 20° C.

Time to produce a rooted cutting (summer): 80 days at 20° C.

Time to produce a rooted cutting (winter): 90 days at 20° C.

Growth rate: Moderate.

Crop time: Approximately 35 to 40 weeks in Sappemeer, Netherlands.

Root system: Fine and fibrous.

Plant fragrance: None.

Branching habit: Leaves arise in basal rosette, no branches.

Foliage:

*Leaf arrangement*.—Basal rosette.

*Compound or single*.—Single.

*Quantity of leaves per plant*.—Average 45.

*Leaf shape*.—Broad lanceolate, succulent.

*Leaf aspect*.—Concave.

*Leaf apex*.—Long apiculate.

*Leaf base*.—Broad cuneate.

*Leaf dimensions*.—13.1 cm. in length, 4.5 cm. in width and 0.7 cm. in thickness.

*Texture* (*both surfaces*).—Pustulate, covered with small orbicular dots, average 0.15 cm. in diameter.

*Leaf luster*.—Upper side glossy, lower side moderately glossy.

*Leaf rugose* (*both surfaces*).—Not rugose.

*Pubescence* (*both surfaces*).—Absent.

*Leaf margin*.—Sharp serrate, teeth 0.1 cm. in length.

*Venation pattern*.—None visible.

*Young leaf color* (*upper surface*).—143A, lighter towards base 143A, dots 147B, margin teeth 157D.

*Young leaf color* (*lower surface*).—In between 141A and 143A, lighter towards base 143A, dots 147B, margin teeth 157D.

*Mature leaf color* (*upper surface*).—In between 139A and 147A, dots 147B, margin teeth 157D.

*Mature leaf color* (*lower surface*).—147A, lighter towards base 143A, dots 147B, margin teeth 157D.

Flower: 'Morombe' has not produced flowers to date.

Fruit and seed: 'Morombe' has not produced fruit or seed to date.

Disease and pest resistance: Disease and pest resistance has not been observed.

The invention claimed is:

1. A new and distinct variety of x*Gasteraloe* plant named 'Morombe' as described and illustrated.

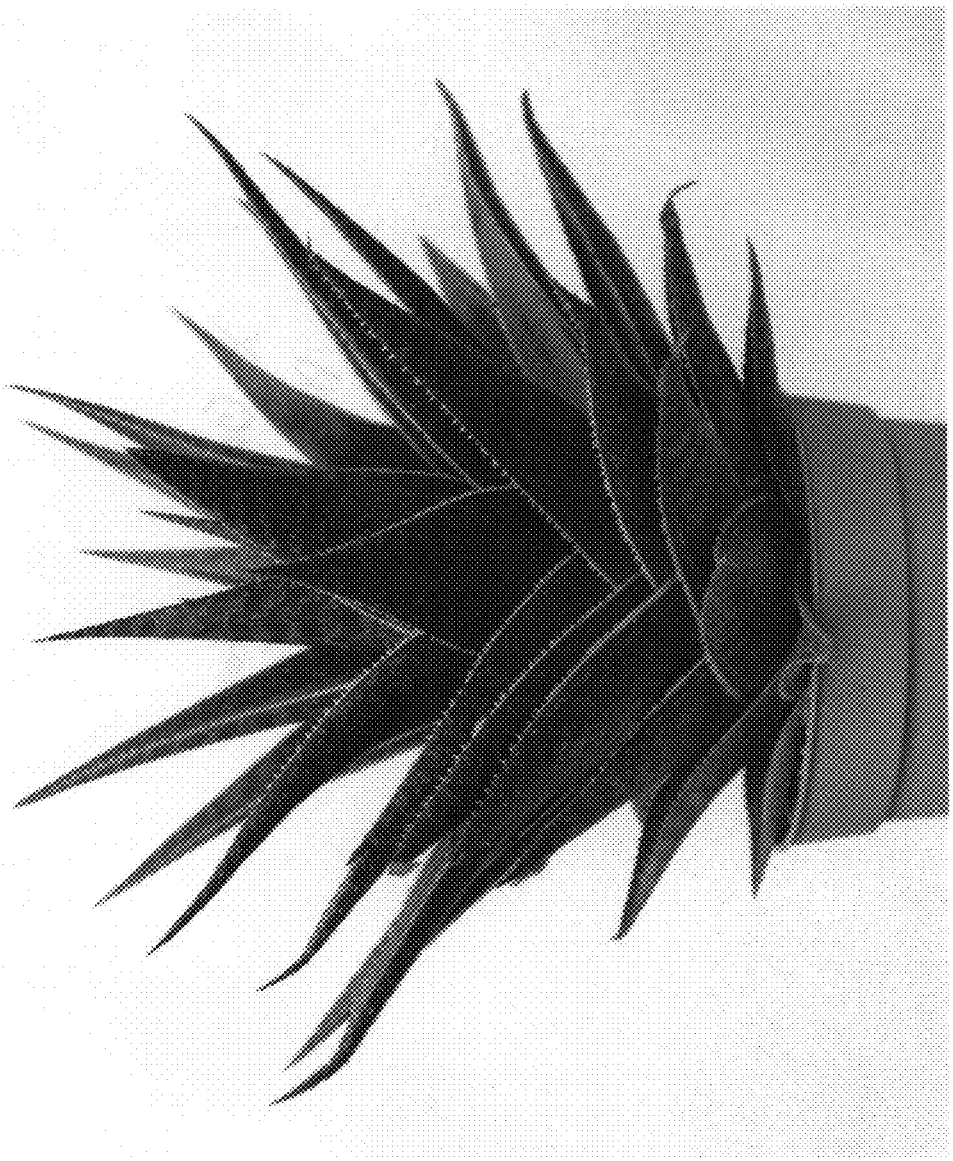

* * * * *